United States Patent [19]
Hider et al.

[11] Patent Number: 5,480,894
[45] Date of Patent: Jan. 2, 1996

[54] 3-HYDROXYPYRIDIN-4-ONE DERIVATIVES AS CHELATING AGENTS

[75] Inventors: Robert C. Hider, Clacton; Surinder Singh, West Croydon; Gary S. Tilbrook, Gerrards Cross; Paul S. Dobbin, Colchester, all of England

[73] Assignee: British Technology Group Limited, London, United Kingdom

[21] Appl. No.: 204,202

[22] PCT Filed: May 18, 1993

[86] PCT No.: PCT/GB93/01007

§ 371 Date: Mar. 7, 1994

§ 102(e) Date: Mar. 7, 1994

[87] PCT Pub. No.: WO94/04498

PCT Pub. Date: Mar. 3, 1994

[30] Foreign Application Priority Data

Aug. 12, 1992 [GB] United Kingdom ............... 9217099

[51] Int. Cl.$^6$ .................... C07D 211/74; A61K 31/44
[52] U.S. Cl. ........................................... 514/348; 546/296
[58] Field of Search ........................... 546/296; 514/348

[56] References Cited

U.S. PATENT DOCUMENTS

| | | | |
|---|---|---|---|
| 4,218,470 | 8/1980 | Casagrande et al. | 514/548 |
| 4,302,471 | 11/1981 | Casagrande et al. | 514/548 |
| 4,585,780 | 4/1986 | Hider et al. | 514/348 |
| 4,650,793 | 3/1987 | Hider et al. | 514/188 |
| 4,908,371 | 1/1990 | Moerker et al. | 514/318 |
| 5,185,319 | 2/1993 | Hider et al. | 514/3 |
| 5,256,676 | 11/1993 | Hider et al. | 514/348 |

FOREIGN PATENT DOCUMENTS

| | | | |
|---|---|---|---|
| 0335745 | 10/1988 | European Pat. Off. | 514/348 |
| 0305646 | 3/1989 | European Pat. Off. | 514/348 |
| 0316279 | 1/1990 | European Pat. Off. | 546/296 |
| 0397409 | 11/1990 | European Pat. Off. | 546/296 |
| 0494754A1 | 7/1992 | European Pat. Off. | 546/296 |
| 2136807 | 9/1984 | United Kingdom | 546/296 |
| 2136806 | 9/1984 | United Kingdom | 546/296 |
| WO89/09211 | 3/1989 | WIPO | 546/296 |

OTHER PUBLICATIONS

Choudhury, R. et al. "Hydrolysis of 1–trimethylacetoxyethyl . . . " Abstract of an oral disclosure given to the UK Association of Pharmaceutical Sciences. Apr. 2–5 1993.
C. Casagrande et al. "Synthesis and Chemical . . . " Simes Res. Lab. Milan, (Italy), pp. 291–303. (1986).
J. B. Porter et al. "Iron Mobilization from . . . " Blood, vol. 72 No. 5 (Nov.) 1988, pp. 1497–1503.
M. C. Brady et al. "Release of Iron . . . " Jour of Inorganic Biochem. 35, (1989), pp. 9–22.
Hider et al. "The inhibition of tyrosinase . . . " Biochemistry (1989) 257, pp. 289–290.
R. O. Epimolu et al. "Chromatography of 3–hydroxypyridin . . . " Jour of Chromatography, 519 (1990), pp. 171–178.
Hider et al. "The development of hydroxypyridin . . . " Annals: New York Acad of Sciences, pp. 327–337. (May 1992).
C. Hershko et al. "New orally effective . . . " Annals of N.Y. Acad of Sci. 1990, 612, pp. 351–360.
S. Whitehead et al. "Differences in the in vitro . . . " 10th Intl Conf on Iron . . . Jul. 27–Jul. 31, 1991., p. 072.
S. Stefanini et al. "The interaction of Hydroxypyridinones . . . " Jour of Inorganic Biochem. 44, (1991), pp. 27–37.
C. Hershko et al. "The effect of N–alkyl . . . " Blood, vol. 77 No. 3 (Feb. 1), 1991, pp. 637–643.
G. J. Kontoghiorghes "Design, properties, and effective . . . " Annals of N.Y. Acad of Sci., 1990, 612, pp. 339–350.
R. C. Hider et al. "Iron chelating agents in medicine . . . " Perspective in Bioinorganic Chemistry, vol. 1 pp. 209–253. (1991).
S. Singh et al. "Urinary Metabolic Profiles . . . " Chelsea Dept of Pharmacy, King's College, London Nov. 19, 1991, pp. 256–261.
C. Hershko et al. "The antimalarial effect of iron chelators . . . " Jour of Inorganic Biochemistry, 47, (1992), pp. 267–277.
S. Singh et al. "Development of 3–hyroxypyridin . . . " The Development of Iron Chelators . . . Gainesville Hilton Hotel, Gainesville, Florida, May 20–22, 1992.

*Primary Examiner*—Alan L. Rotman
*Attorney, Agent, or Firm*—Nixon & Vanderhye

[57] ABSTRACT

3-Hydroxypyridin-4-ones of formula (I)

in which $R_1$ is a methyl, ethyl, 2-($\alpha$-methylpropionyloxy)ethyl or 2-pivoloyloxyethyl group and $R_2$, $R_3$ and $R_4$ are each separately selected from hydrogen and methyl, ethyl, 2-($\alpha$-methylpropionyloxy)ethyl and 2-pivaloyloxyethyl groups with the provisos that (a) one only of $R_1$ to $R_4$ is either a 2-($\alpha$-methylpropionyloxy)ethyl group or a 2-pivaloyloxyethyl group, (b) at least one of $R_2$ and $R_3$ is other than hydrogen and (c) the total number of carbon atoms in $R_1$ to $R_4$ is no more than eleven, and physiologically acceptable salts thereof are of use in therapy, particularly in the treatment of conditions in which there is a toxic concentration of a metal, for example iron, in the body.

22 Claims, No Drawings

3-HYDROXYPYRIDIN-4-ONE DERIVATIVES AS CHELATING AGENTS

CONTINUING DATA

This application is a 371 of PCT1GB 93/01007 filed May 18, 1993.

This invention relates to novel 3-hydroxypyridin-4-one chelating agents of therapeutic value, the compounds being of particular value in the treatment of conditions in which there is a toxic concentration of a metal, for example iron, in the body.

UK Patent No. 2 136 807 and various scientific papers describe the use of 3-hydroxypyridin-4-ones for the treatment of iron overload arising from various causes, particularly that arising from pathological conditions such as thalassaemia, sickle cell anaemia, aplastic anaemia, and idiopathic haemochromatosis, often through the treatment of the first three conditions by regular blood transfusions. Moreover, in addition to use for the treatment of general iron overload, the 3-hydroxpyridin-4-ones are of interest for use in certain pathological conditions where there may be an excess of iron deposited at certain sites even though the patient does not exhibit a general iron overload, this being the case, for example, in certain arthritic and cancerous conditions.

Although the major use described in the literature for these compounds is in the removal of iron, they are also of potential interest for the removal of other metals present in the body in deleterious amounts, for example copper, plutonium and other related transuranic metals, and especially aluminium.

The 3-hydroxypyridin-4-ones are also of interest for use in certain other contexts. Thus the free 3-hydroxypyridin-4-ones have been proposed for use in the treatment of inflammatory and atherosclerotic disease, of neoplastic disease, and as platelet anti-aggregatory agents with a role in the treatment of thrombosis. They are also of interest in various areas where chelating agents can be of value, for example in the treatment of paraquat poisoning.

We have now found that a small group of 3-hydroxypyridin-4-ones falling within the scope of UK Patent No. 2 136 807 but not specifically disclosed therein has properties which render these 3-hydroxypyridin-4-ones particularly suitable for use in the treatment of iron overload.

Accordingly the present invention comprises a compound being a 3-hydroxypyridin-4-one of formula (I)

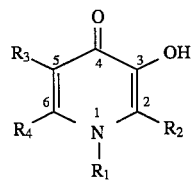

(I)

in which $R_1$ is a methyl, ethyl, 2-(α-methylpropionyloxy)ethyl or 2-pivaloyloxyethyl group and $R_2$, $R_3$ and $R_4$ are each separately selected from hydrogen and methyl, ethyl, 2-(α-methylpropionyloxy)ethyl and 2-pivaloyloxyethyl groups with the provisos that (a) one only of $R_1$ to $R_4$ is either a 2-(α-methylpropionyloxy)ethyl group or a 2-pivaloyloxyethyl group, (b) at least one of $R_2$ and $R_3$ is other than hydrogen and (c) the total number of carbon atoms in $R_1$ to $R_4$ is no more than eleven, the compound optionally being in the form of a physiologically acceptable salt.

We have found that the selection of a particularly suitable chelating agent for the oral treatment of iron overload presents two contradictory requirements in as far as it is desirable firstly that the agent used is efficient at entering the bloodstream and thus the liver from the gastrointestinal tract and secondly that it is not efficient at crossing the blood-brain barrier. It is difficult to reconcile these two requirements. Proposals have been made in European Patent Application 0316279A to modify the 3-hydroxy group of the 3-hydroxypyridin-4-ones to provide a pro-drug form, i.e. in the form of a drug which does not itself possess the desired biological activity but which is converted in vivo to a drug which does. The 3-hydroxypyridin-4-ones highlighted in that patent application do, however, have alkyl and alkoxyalkyl substituents and are themselves therefore quite efficient both at entering the bloodstream and at crossing the blood-brain barrier so that the formulation of these compounds in a pro-drug form which enhances entry to the bloodstream but does not effect crossing of the blood-brain barrier is not directed towards overcoming the basic difficulty.

By way of contrast, the compounds of the present invention are not true pro-drugs since they are themselves active as chelating agents. However, following their ready entry into the bloodstream from the gastrointestinal tract the compounds are metabolised, particularly in the liver, with the conversion of the 2-(α-methylpropionyloxy)ethyl or 2-pivaloyloxyethyl group to a 2-hydroxyethyl group. The metabolites containing a 2-hydroxyethyl group undergo phase 1 metabolism very slowly and these 3-hydroxypyridin-4-ones substituted by such a group and by one or more methyl or ethyl groups as described hereinbefore, unlike the parent 2-(α-methylpropionyloxy)ethyl or 2-pivaloyloxyethyl compounds, are not efficient at crossing the blood-brain barrier.

The present invention thus provides a group of 3-hydroxypyridin-4-ones which are particularly adapted for therapeutic use in vivo, especially for the treatment of iron overload.

The compounds of formula (I) contain a single 2-(α-methylpropionyloxy)ethyl [$(CH_3)_2CHCOOCH_2Ch_2$—] or 2-pivaloyloxyethyl [$(CH_3)_3CCOOCH_2CH_2$—] group and this is preferably the group $R_2$ or particularly the group $R_1$. The compounds containing a 2-pivaloyloxyethyl group are preferred to those containing a 2-(α-methylpropionyloxy)ethyl group in view of the greater stability of the pivaloyloxy group in the gastrointestinal tract. However, once a compound has entered the bloodstream the greater ease of metabolism of compounds containing an α-methylpropionyloxy group does mean that such compounds are nevertheless of interest.

It is required that at least one of $R_2$ and $R_3$ is other than hydrogen and it is preferred that this is $R_2$ with $R_3$ preferably being hydrogen. The total number of carbon atoms in $R_1$ to $R_4$ is no more than eleven, so that the corresponding 2-hydroxyethyl compound contains no more than six carbon atoms when derived from a compound containing a 2-pivaloyloxyethyl group and no more than seven carbon atoms when derived from a compound containing a 2-(α-methylpropionyloxy)ethyl group. Advantageously, however, the total of carbon atoms in the groups $R_1$ to $R_4$ of the compound of formula (I) is no more than ten or particularly nine. Thus it is preferred that apart from the group which is the 2-(α-methylpropionyloxy)ethyl or 2-pivaloyloxyethyl group the other groups of $R_1$ to $R_4$ are one hydrogen and two methyl groups, more particularly two hydrogen and one methyl group, or especially two hydrogen and one ethyl group.

Specific compounds of especial interest are thus, in increasing order of interest:

1) 3-hydroxy-2,6-dimethyl-1-(2-pivaloyloxyethyl)pyridin-4-one;
2) 3-hydroxy-1-methyl-2-(2-pivaloyloxyethyl)pyridin-4-one;
3) 1-ethyl-3-hydroxy-2-(2-pivaloyloxyethyl)pyridin-4-one;
4) 3-hydroxy-2-methyl-1-(2-pivaloyloxyethyl)pyridin-4-one; and
5) 2-ethyl-3-hydroxy-1-(2-pivaloyloxyethyl)pyridin-4-one;

as well as the analogues of these compounds in which the 2-pivaloyloxyethyl group is replaced by a 2-(α-methylpropionyloxy)ethyl group.

The compounds may, if desired, be used in the form of a physiologically acceptable salt. These salts may be of two types, being formed with either physiologically acceptable bases or acids. Thus salts may be formed between the anion produced by the loss of the 3-hydroxy group proton and a base derived cation. Examples of suitable bases are the alkali metal hydroxides, for example sodium hydroxide, quaternary ammonium hydroxides and amines such as tris (tris representing 2-amino-2-hydroxymethyl propane 1,3-diol). More preferably, salts may be formed through protonation of the carbonyl function at the 4-position of the 3-hydroxypyridinone ring by an acid. Suitable acids may be inorganic or organic. Examples of such inorganic acids are phosphoric acid, nitric acid, sulphuric acid and particularly the hydrohalic acids hydrochloric acid, hydrobromic acid and hydroiodic acid. Examples of such organic acids are citric acid, oxalic acid, fumaric acid, maleic acid, lactic acid, succinic acid, malic acid, tartaric acid and methane sulphonic acid.

The compounds (I) may conveniently be prepared starting from the corresponding 2-hydroxyethyl substituted 3-hydroxypyrid-4-one. Such intermediates may be prepared by procedures such as those described in UK Patent GB 2 136 807B and by variations thereon which will be apparent to those skilled in the art. In particular a corresponding 3-hydroxy-4-pyrone can be reacted with a compound R'NH$_2$ in which R' represents the group present on the nitrogen atom of the desired compound or a group convertible thereto, the reaction being carried out in the presence of a base, for example an alkali metal hydroxide such as sodium hydroxide. This procedure is specifically exemplified in Example 11 of GB 2 136 807B for the preparation from maltol of 3-hydroxy-1-(2-hydroxyethyl)-2-methylpyridin-4-one, which is obtained by the procedure described in that patent in the form of the hydrobromide, and may be applied in an exactly analogous fashion to the preparation of other compounds (I) of the present invention having alternative groups R$_1$ to R$_4$.

Other 3-hydroxy-4-pyrone starting materials than maltol are readily available, for example as described in published U.S. patent application Ser. No. 310,141 (series of 1960) or otherwise. As regards the pyrones having a (2-hydroxyethyl) group at other than the 1-position, the 2-(2-hydroxyethyl) compounds, for example, may be prepared from the corresponding 2-hydroxymethyl compound (itself preparable by the condensation of the corresponding 3-hydroxy-4-pyrone with formaldehyde) in which the 3-hydroxy group is protected by benzylation, through bromination of the remaining hydroxy group, formation of a Grignard reagent, and reaction thereof with carbon dioxide to give the 2-carboxymethyl compound. Reduction firstly with lithium aluminium hydride converts the 2-carboxymethyl group to a 2-(2-hydroxyethyl) group and then with hydrogen over palladium removes the benzyl protecting group. In the event of the degree of lysis of the pyran ring by the LiAlH$_4$ being unacceptable the series of reactions can instead be carried out on a 3-hydroxy-2-hydroxymethypyridin-4-one in which the 3-hydroxy group is protected by benzylation and the nitrogen atom carries the desired N-substituent or a group which is convertible thereto either directly or through its removal to regenerate an NH group and the subsequent substitution thereof.

An alternative general route to (2-hydroxyethyl)-substituted 3-hydroxypyrid-4-ones involves nucleophilic substitution at the nitrogen atom of the corresponding 3,4-dihydroxypyridine (or 3-hydroxypyridin-4-one), for example using an organic halide R'X in which R' represents the group present on the nitrogen atom of the desired compound or a group convertible thereto. Yet another route involves reaction of the corresponding 3-hydroxypyridin-4-one with an amine R'NH$_2$ in which R' represents the group present on the nitrogen atom of the desired compound or a group convertible thereto.

In most cases it will be appropriate to protect the 3-hydroxy group in the reactant 3-hydroxypyrone or 3-hydroxypyridinone precursor. A common form of protection is to convert the 3-hydroxy group to a benzyloxy group which can eventually be reconverted to a free hydroxy group by catalytic hydrogenation. Moreover, as indicated, it may be appropriate for a substituent group in the initially formed 3-hydroxypyridin-4-one to be modified to provide the desired substituents.

Two main alternative procedures are available for the conversion of the (2-hydroxyethyl)-substituted intermediates to the corresponding [2-(α-methylpropionyloxy)ethyl] or (2-pivaloyloxyethyl) compounds. Firstly, an intermediate 3-hydroxypyridin-4-one substituted by a (2-hydroxyethyl) group may be esterified under conditions appropriate to effect selective esterification of only the hydroxy group of the (2-hydroxyethyl) group.

Secondly, the intermediate may be converted to a derivative thereof in which the hydroxy group of the (2-hydroxyethyl) group is converted to a [2-(α-methylpropionyloxy)ethyl] or (2-pivaloyloxyethyl) group and the 3-hydroxy group is also derivativized. Thus, for example, an intermediate having a 3-benzyloxy group such as 3-benzyloxy-1-(2-hydroxyethyl)-2-methylpyridin-4-one may be esterified using an appropriate agent, for example pivaloyl chloride, pivalic anhydride, an activated pivalic ester, pivalic acid in the presence of an appropriate reagent such as dicyclohexylcarbodiimide, etc., or the equivalent reagent containing a (CH$_3$)$_2$CH rather than a (CH$_3$)$_3$C grouping, and the protecting benzyl group then removed, for example using hydrobromic acid or by hydrogenation. In an alternative, preferred procedure an intermediate 3-benzyloxypyridin-4-one substituted by a (2-hydroxyethyl) group is esterified at both the hydroxy groups of the (2-hydroxyethyl) group and the protected 3-hydroxy group by the same reagent, when the 3-benzyloxy group is converted to a 3-α-methylpropionyloxy or 3-pivaloyloxy group. The esterified 3-hydroxy group is then selectively hydrolysed, for example with dilute aqueous acetic acid of pH 4.0 at room temperature or with water at 70° C. to yield the required [2-(α-methylpropionyloxy)ethyl] or (2-pivaloyloxyethyl) compound of formula (I). In both cases, the esterification may conveniently be effected by the use of α-methylpropionyl chloride or pivaloyl chloride as the esterifying agent in the presence of a base such as triethylamine but using somewhat different conditions as described in Examples 2 and 3, and 4 and 5 hereinafter to produce mono- or di-esterification.

Salts may readily be formed by reaction of the compound (I) with the appropriate base or acid under suitable conditions. Thus, freeze drying of an aqueous solution whose pH has been adjusted to about 11 with the desired base provides a convenient route to a salt of that base containing an anion formed by the loss of the 3-hydroxy group proton. Salts with acids may conveniently be obtained by recrystallization of the compound (I) from an aqueous/organic solution, for example the hydrochloride being obtained on recrystallization from a dilute hydrochloric acid/ethanol solution.

The compounds (I) may be formulated with a physiologically acceptable diluent or carrier for use as pharmaceuticals for veterinary, for example in a mammalian context, and particularly for human use by a variety of methods. For instance, they may be applied as a composition incorporating a liquid diluent or carrier, for example an aqueous or oily solution, suspension or emulsion, which may be employed in injectable form if parenteral administration is used, therefore conveniently being sterile and pyrogen free. Oral administration is, however, preferred. Although compositions for this purpose may incorporate a liquid diluent or carrier, it is more usual to use a solid, for example a conventional solid carrier material such as starch, lactose, dextrin or magnesium stearate. Such solid compositions may conveniently be of a formed type, for example as tablets, capsules (including spansules), etc.

Other forms of administration than by injection or through the oral route may also be considered in both human and veterinary contexts, for example the use of suppositories or pessaries. Another form of pharmaceutical composition is one for buccal or nasal administration, for example lozenges, nose drops or an aerosol spray.

Thus, the invention further includes a pharmaceutical composition comprising a 3-hydroxypyridin-4-one of formula (I) as defined hereinbefore together with a physiologically acceptable diluent or carrier.

Compositions may be formulated in unit dosage form, i.e. in the form of discrete portions each comprising a unit dose, or a multiple or sub-multiple of a unit dose. Whilst the dosage of active compound given will depend on various factors, including the particular compound which is employed in the composition and the mode of administration and the nature of the condition being treated, it may be stated by way of guidance that satisfactory control of the amount of iron present in the human body will often be achieved using a daily dosage of about 10 to 100 mg/kg, particularly 20 to 50 mg/kg, for example 25 mg/kg, of the compound of formula (I), veterinary doses being on a similar g/kg body weight ratio. Similar dosages are also suitable for the removal of other metals present in the body in deleterious amounts.

Where desired, more than one compound according to the present invention may be administered in the pharmaceutical composition, when the total dosage will usually correspond to those discussed above, or, indeed, other active compounds may be included in the composition.

The present invention therefore includes a method for the treatment of a patient having a condition requiring treatment by a chelating agent, for example a toxic concentration of iron present in the body, which comprises administering to that patient a therapeutically effective amount of a compound of formula (I) as defined hereinbefore.

The invention is illustrated by the following Examples.

EXAMPLES

Example 1: Preparation of 3-hydroxy-2-methyl-1-(2-pivaloyloxyethyl) pyridin-4-one (1) 3-Benzyloxy-2-methyl-4-pyrone A solution of sodium hydroxide (126 g, 1.1 mol) in 1000 ml of methanol in water (9:1 v/v) was added to 3-hydroxy-2-methyl-4-pyrone (126.12 g, 1 mol). Benzyl chloride (126.59 ml, 1.1 mol) was then added slowly and the mixture was refluxed for 10 hours with rapid stirring. The resultant solution was cooled, the methanol removed by rotary evaporation and the aqueous solution was extracted with dichloromethane (3×250 ml). The combined dichloromethane extracts were washed with 5% sodium hydroxide and then with water, dried over anhydrous sodium sulphate, filtered and evaporated to dryness. The resultant solid was recrystallised from diethylether to yield the title compound in 76.8% yield as colourless needles, m.p. 53°–55° C.

(2) 3-Benzyloxy-1-(2-hydroxyethyl)-2-methylpyridin-4-one

A solution of the product from (1) in ethanol:water (300 ml:300 ml) containing 5% aqueous sodium hydroxide (2 ml) was treated with ethanolamine (17 ml) and then refluxed for 18 hours with rapid stirring. The resultant solution was cooled and adjusted to pH 1 with concentrated hydrochloric acid. The solid which formed on cooling was extracted with hot absolute ethanol and the precipitate obtained on cooling was taken up in diethylether, the solution being filtered and evaporated to dryness by rotary evaporation to give the title compound in 44.94% yield, m.p. 191.5°–193° C.

(3) 3-Benzyloxy-2-methyl-1-(2-pivaloyloxyethyl)pyridin-4-one

Trimethylamine (4.7 ml) was added with stirring to a solution of 3-benzyloxy-1-(2-hydroxyethyl)-2-methylpyridin-4-one (2 g) in dimethylformamide (40 ml) and the solution was then heated under reflux while pivaloyl chloride (1 ml) was added dropwise. The mixture was refluxed at 78° C. for two hours whilst monitoring by thin layer chromatography (1:1 v/v ethyl acetate:methanol) when very little change of the mixture was obtained. Further trimethylacetylchloride (3 ml) was therefore added and refluxing continued for another 16 hours. The solution was evaporated to dryness, the resultant solid was dissolved in dichloromethane (100 ml) and this solution was washed with sodium bicarbonate solution (0.05M, 4000 ml) and the organic phase was then dried over anhydrous sodium sulphate, filtered and evaporated to dryness. The resultant crude product was flash chromatographed (silica gel, Kieselgel 60,7754, 20 mm×300 mm column; eluting with acetonitrile:ethyl acetate, 1:9 v/v) to provide the title compound in 60% yield as a colourless solid, m.p. 103°–105.8° C.

(4) 3-Hydroxy-2-methyl-1-(2-pivaloyloxyethyl)pyridin-4-one

3-Benzyloxy-2-methyl-1-(2-pivaloyloxyethyl)pyridin-4-one (1.08 g, 0.003 mol) was hydrogenated over Pd/C catalyst in dimethylformamide (30 ml) with stirring for 24 hours. The solution was filtered and rotary evaporated to dryness to provide a crude product (1.08 g) which was flash chromatographed (silica gel, Kieselgel 60,7734, 20 mm×300 mm column, eluting with ethyl acetate:ethanol, 1:1 v/v). Rotary evaporation in vacuo at 60° C. provided the title compound in 77.46% yield as orange crystals, m.p. 147°–149° C.; $v_{max}$ 1580, 1625, 1725, 2850 cm$^{-1}$; $\delta(d_6$ dimethylsulphoxide) 1.1 (9H,s), 2.35 (3H,s), 4.30 (4H,s), 4.4 (1H,s), 6.15 (1H,d), 7.55 (1H,d).

Example 2: Preparation of 2-ethyl-3-hydroxy-1-(2-pivaloyloxyethyl)-pyridin-4-one (1) 3-Benzyloxy-2-ethyl-4-pyrone To a suspension of 2-ethyl-3-hydroxy-4-pyrone (70 g, 0.5 mol) in methanol (650 ml) and sodium hydroxide solution (24 g, 0.6 mol of sodium hydroxide dissolved in 80 ml distilled water) was added benzyl chloride (90 ml, 0.75 mol) with stirring at room temperature. The reaction mixture was refluxed for 24 hours and then cooled. The solvent was removed by rotary evaporation and the residue was extracted into dichloromethane (500 ml). The organic layer was washed with 5% w/v sodium hydroxide solution (3×600 ml) and water (2×600 ml), dried over anhydrous sodium sulphate, filtered and rotary evaporated to give an oil. This oil was crystallized from diethylether in liquid nitrogen and the product recrystallized from diethylether to give the title compound (69 g, 65%) as colourless crystals, m.p. 33°–34° C.

(2) 3-Benzyloxy-1-(2-hydroxyethyl)-2-ethylpyridin-4-one hydrochloride

To a suspension of 3-benzyloxy-2-ethyl-4-pyrone (10.5 g, 0.05 mol) in ethanol (150 ml) and water (200 ml) was added ethanolamine (6.7 ml, 0.11 mol). The reaction mixture was adjusted to pH 13 by the addition of sodium hydroxide solution (10M) and was then refluxed for 48 hours.

When the reaction was complete, the solvent was removed by rotary evaporation and the volume reduced to 50 ml. The resultant solution was diluted with water (100 ml), cooled and adjusted to pH 7 by the addition of concentrated hydrochloric acid. The reaction mixture was extracted with dichloromethane (3×100 ml) and the organic extracts were dried over anhydrous sodium sulphate, filtered and rotary evaporated to give an oil. This oil was dissolved and the solution treated with hydrochloric acid. The resultant precipitated solid was dissolved in hot ethanol and recrystallized by the addition of diethylether to give the title compound (8 g, 57%) as colourless crystals, m.p. 165°–167° C.

(3) 3-Benzyloxy-2ethyl-1-(2-pivaloloxyethyl)pyridin-4-one

To a solution of 3-benzyloxy-2-ethyl-1-(2-hydroxyethyl)pyridin-4-one hydrochloride (0.46 g, 0.0015 mol) in tetrahydrofuran (30 ml) and dichloromethane (5 ml) was added triethylamine (1 ml, 0.0075 mol) and the mixture stirred for 10 minutes. Pivaloyl chloride (0.37 ml, 0.003 mol) was added dropwise to the warm reaction mixture which was then heated at 60° C. for a further 24 hours. The solvent was removed by rotary evaporation and the residue extracted with dichloromethane (50 ml), the solution being washed with aqueous sodium bicarbonate (5% w/v, 3×40 ml). The organic layer was dried, filtered and rotary evaporated to give an oil which was chromatographed on a column of silica gel eluting with 9:1 v/v $CHCl_3:CH_3OH$. Evaporation of the solvent gave the title compound as an oil (0.5 g, 87%) from which was obtained a crystalline solid, m.p. 173°–175° C. $\delta$(60 MHz, $CDCl_3$), 7.3 (5H, m), 7.15 (1H, d), 6.33 (1H, d), 5.2 (2H, s), 4.15 (2H, t), 4.05 (2H, t), 2.55 (2H, q), 1.1 (9H, s), 1 (3H, t).

(4) 2-Ethyl-3-hydroxy-1-(2-pivaloyloxyethyl)pyridin-4-one

To a solution of 3-benzyloxy-2-ethyl-1-(2-pivaloyloxyethyl)pyridin-4-one (0.5 g) in dimethylformamide (25 ml) was added 5% palladium on charcoal catalyst (0.1 g) and the reaction mixture was stirred at room temperature under a constant stream of hydrogen for 24 hours. The dimethylformamide was then removed under high vacuum by rotary evaporation to give an oil. The solid obtained on cooling the oil was dissolved in hot ethyl acetate and the solution treated with activated charcoal, refluxed for 5 minutes, filtered and rotary evaporated. The resultant residue was recrystalized from petroleum ether (boiling point 40°–60° C.) to give the title compound (2 g, 53%) as colourless crystals, m.p. 113°–115° C., $v_{max}$ (nujol) 1580, 1630, 1725, 3130 $cm^{-1}$; $\delta$(90 MHz, $CDCl_3$), 7.25 (1H, d), 6.43 (1H, d), 5.25 (1H, s, br), 4.29 (2H, t), 4.21 (2H, t), 2.85 (2H, q), 1.27 (3H, t), 1.28 (9H, s).

Example 3: Preparation of 2-ethyl-3-hydroxy-1-(2-pivaloyloxyethyl)pyridin-4-one (1) 2-Ethyl-3-pivaloyloxy-1-(2-pivaloyloxethyl)pyridin-4-one To a solution of 3-benzyloxy-2-ethyl-1-(2-pivaloyloxyethyl)pyridin-4-one hydrochloride (3 g, 0.01 mol; prepared as described in Example 2) in dimethylformamide (60 ml) was added triethylamine (7 ml, 0.05 mol). The solution was stirred for 10 minutes, pivaloyl chloride (4.9 ml, 0.04 mol) was then added dropwise to the warm solution and the reaction mixture was heated further at 78° C. overnight.

The dimethylformamide was then removed by rotary evaporation under high vacuum and the residue was extracted with dichloromethane (100 ml). The organic solution was washed with aqueous sodium bicarbonate (5% w/v, 3×40 ml) and the organic layer was dried, filtered and rotary evaporated to give an oil which was chromatographed on a column of silica gel eluting with 9:1 v/v $CHCl_3:CH_3OH$. Evaporation of the solvent gave an oil which solidified. Recrystallization of the solid product from ethyl acetate and petroleum ether (b.p. 40°–60° C.) gave the title compound (2.5 g, 71%) as colourless crystals, m.p. 138°–139° C., $v_{max}$ (nujol) 1587, 1630, 1725, 1740 $cm^{-1}$.

(2) 2-Ethyl-3-hydroxy-1-(2-pivaloyloxyethyl)pyridin-4-one

2-Ethyl-3-pivaloyloxy-1-(2-pivaloyloxyethyl)pyridin-4-one (0.5 g) was heated in distilled water (40 ml) at 70° C. for 3 hours. The water was removed by rotary evaporation and the residue dried under high vacuum. Recrystallization of the dry solid from ethyl acetate and petroleum ether (b.p. 40°–600° C.) gave the title compound (0.3 g, 69%) as colourless crystals with a melting point and infra-red and n.m.r. spectra as quoted in Example 2.

Example 4: Preparation of 2-ethyl-3-hydroxy-1-[2-(α-methylpropionyloxy)ethyl]pyridin-4-one (1) 2-Ethyl-3-α-methylpropionyloxy)-1-[2-(α-methlpropionyloxy)ethyl]pyridin-4-one To a solution of 3-benzyloxy-2-ethyl-1-(2-hydroxyethyl)pyridin-4-one hydrochloride (3.1 g, 0.01 mole; prepared as described in Example 2) in 100 ml of dry dimethylformamide was added dropwise triethylamine (7 ml, 0.05 mole) whilst stirring over 15 minutes under $N_2$. Isobutyryl chloride (4.2 ml, 0.04 mole) was then added dropwise and the mixture was heated at 75°–78° C. overnight under $N_2$. The reaction was monitored by tlc (silica; 50% EtOH:50% EtOAc) and after filtration the dimethylformamide was removed under high vacuum by rotary evaporation. The solid residue was dissolved in 100 ml of dichloromethane and washed with 5% w/v aqueous $NaHCO_3$ (3×100 ml) and water (2×100 ml). The organic layer was dried over $Na_2SO_4$, filtered and rotary evaporated to give a crude solid. Purification was achieved by recrystallization using activated charcoal in ethyl acetate. The filtrate was used for further crystallization of the solid from ethyl acetate to give the title compound in 40% yield, $\delta$(DMSO): 0.8–1.12 (15H, m), 2.3–2.8 (4H, m), 4.15 (4H, s), 5.9–6.1 (1H, d, 7 Hz), 7.5–7.7 (1H, d, 8 Hz).

(2) 2-Ethyl-3-hydroxy-1-[2-(α-methlpropionyloxy)ethyl]pyridin-4-one

2-Ethyl-3-α-methylpriopionyloxy-1-[2-(α-methylpropionyloxy)ethyl]pyride-4-one (1.2 g) was dissolved in 60 ml of distilled water and heated at a temperature of 65°–70° C., for 2 hours. The reaction was monitored by tlc (silica; 50% EtOH:50% EtOAc) and after the 2 hours the solution was rotary evaporated to dryness. The solid residue was recrystallized from ethyl acetate/petroleum ether (b.p. 60°–80° C.) to give the title compound in 59% yield, m.p. 106°–108° C., $v_{max}$ (nujol), 1610, 1720, 3440 cm$^{-1}$; δ(DMSO) 0.9–1.2 (9H, m), 2.3–2.9 (3H, m), 4.15 (4H, s), 5.9–6.1 (1H, d 7 Hz), 7.3–7.5 (1H, d, 7 Hz); M$^+$ 253.

Example 5: Preparation of 2-ethyl-3-hydroxy-1-[2-(α-methylpropionyloxy)ethyl]pyridin-4-one (1) 3-Benzyloxy-2-ethyl-1-[2-(α-methylpropionyloxy)ethyl]pyridin-4-one 3-Benzyloxy-2-ethyl-1-(2-hydroxyethyl)pyridin-4-one (0.92 g, 0.003 mole, prepared as described in Example 2), was dissolved in a mixture of 30 ml dimethylformamide and 20 ml of pyridine at room temperature whilst stirring under $N_2$. The solution was added dropwise to a mixture of isobutyryl chloride (1.3 ml, 0.012 mole) in 10 ml of pyridine at 0° C. and the resulting solution was then stirred at room temperature overnight under $N_2$. The reaction was monitored by tlc (silica; 50% EtOH:50% EtOAc). The solution was filtered, the dimethylformamide was removed under high vacuum by rotary evaporation and the oily residue was dissolved in 100 ml of dichloromethane. The solution was washed with 5% w/v aqueous $NaHCO_3$ (3×100 ml) and water (2×100 ml). The organic layer was dried over $Na_2SO_4$, filtered and rotary evaporated to give a crude oil. This was treated with activated charcoal in ethyl acetate, filtered and rotary evaporated. The oil produced was purified by means of column chromatography (silica; 50% EtOH:50% EtOAc). Rotary evaporation of the selected samples gave the title compound as an oil in 66% yield, δ(CDCl$_3$), 0.9–1.3 (9H, m), 2.3–2.7 (3H, m), 3.5–4.3 (4H, m), 5.2 (2H, s), 6.2–6.4 (1H, d, 7 Hz), 7.1–7.5 (6H, m).

(2) 2-ethyl-3-hydroxy-1-[2-(α-methylpropionyloxy)ethyl]pyridin-4-one

3-Benzyloxy-2-ethyl-1-[2-(α-methylpropionyloxy)ethyl]pyridin-4-one was dissolved in 35 ml of dimethylformamide and about 0.1 g of palladium on activated charcoal (5%) was added. The solution was left under $H_2$ for four days and the reaction was monitored by tlc (silica; 50% EtOH:50% EtOAc). The solution was filtered three times and rotary evaporated under high vacuum. The oily residue was then treated with activated charcoal in ethyl acetate, filtered and rotary evaporated to dryness. After crystallization from ethyl acetate the pure title compound was obtained in 37% yield, m.p., i.r., n.m.r. and mass spectra as quoted in Example 4.

Example 6: Partition data

The partition coefficients of four or five samples of each of the compounds of Examples 2 and 4 were measured using essentially the procedure described in Example 25 of UK Patent No. 2 136 807. For comparative purposes a similar measurement was made for the compound 1-(2-acetoxyethyl)-2-ethyl-3-hydroxypyridin-4-one which was prepared by an analogous procedure to that of Example 5 using acetyl chloride in place of isobutyryl chloride. The results obtained for the partition coefficient $K_{part}$, being the ratio (concentration of compound in n-octanol)/concentration of compound in aqueous phase on partition between n-octanol and aqueous tris hydrochloride (20 mM, pH 7.4), are shown in the Table.

TABLE

| Sample | Compound (ester group) | | |
|---|---|---|---|
| | (CH$_3$)$_3$CCOO | (CH$_3$)$_2$CHCOO | CH$_3$COO |
| 1 | 5.104 | 5.005 | 1.500 |
| 2 | 7.992 | 4.541 | 0.948 |
| 3 | 3.870 | 4.224 | 0.940 |
| 4 | 6.742 | 4.797 | 0.962 |
| 5 | 6.855 | — | — |
| Mean ± S.E. | 6.113 ± 1.622 | 4.642 ± 0.337 | 1.088 ± 0.275 |

Example 7: Formulation of medicaments (A) Tablets of the following composition are prepared:

| | mg/tablet |
|---|---|
| 2-ethyl-3-hydroxy-1-(2-pivaloyloxyethyl)-pyridin-4-one (micronised) | 250 |
| 'Avicel' (microcrystalline cellulose) | 38 |
| polyvinylpyrrolidone | 3 |
| alginic acid | 6 |
| magnesium stearate | 3 |

The 3-hydroxypyridin-4-one is mixed with 'Avicel' and polyvinylpyrrolidone is added, dissolved in sufficient industrial methylated spirits (74° OP) to produce a mass suitable for granulating. The mass is granulated through a 20 mesh sieve and the resultant granules are dried at a temperature not exceeding 50° C. The dried granules are passed through a 20 mesh sieve and the alginic acid and magnesium stearate are then added and mixed with the granules. The product is compressed into tablets each weighing 300 mg on ⅜ inch flat bevelled edge divided punches.

(B) Tablets of the following composition are prepared:

| | mg/tablet |
|---|---|
| 2-ethyl-3-hydroxy-1-(2-pivaloyloxyethyl)-pyridin-4-one (micronised) | 250 |
| 'Avicel' (microcrystalline cellulose) | 134 |
| polyvinylpyrrolidone | 4 |
| alginic acid | 8 |
| magnesium stearate | 4 |

The tablets are prepared by essentially the same procedure as described in (A) and are compressed at a tablet weight of 400 mg on 7/16 inch flat bevelled edge punches.

(C) Tablets of the following composition are prepared:

| | mg/tablet |
|---|---|
| 2-ethyl-3-hydroxy-1-(2-pivaloyloxyethyl)-pyridin-4-one (micronised) | 250 |
| lactose (300 mesh) | 19 |
| maize starch | 15 |
| gelatine | 10 |
| magnesium stearate | 6 |

The 3-hydroxypyridin-4-one is mixed with lactose and half the total quantity of maize starch required, and a 5% solution of gelatine in water is added to the mass. The product is granulated through a 16 mesh sieve, and the resultant granules are dried to constant weight at a temperature not exceeding 50° C. The dried granules are passed through a 20 mesh sieve and mixed with magnesium stearate and the remainder of the maize starch. The product is compressed at a 300 mg tablet weight on ⅜ inch flat bevelled edge divided punches.

Similar procedures may be followed with other compounds such as that of Example 1 or 4.

We claim:

1. A compound being a 3-hydroxypyridin-4-one of formula (I)

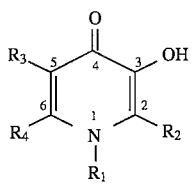

in which $R_1$ is a methyl, ethyl, 2-(α-methylpropionyloxy)ethyl or 2-pivaloyloxyethyl group and $R_2$, $R_3$ and $R_4$ are each separately selected from hydrogen and methyl, ethyl, 2-(α-methylpropionyloxy)ethyl and 2-pivaloyloxyethyl groups with the provisos that (a) one only of $R_1$ to $R_4$ is either a 2-(α-methylpropionyloxy)ethyl group or a 2-pivaloyloxyethyl group, (b) at least one of $R_2$ and $R_3$ is other than hydrogen and (c) the total number of carbon atoms in $R_1$ to $R_4$ is no more than eleven, the compound optionally being in the form of a physiologically acceptable salt.

2. A compound according to claim 1, in which $R_2$ is a 2-(α-methylpropionyloxy)ethyl or 2-pivaloyloxyethyl group.

3. A compound according to claim 1, in which $R_1$ is a 2-(α-methylpropionyloxy)ethyl or 2-pivaloyloxyethyl group.

4. A compound according to claim 1, which contains one 2-pivaloyloxyethyl group rather than one 2-(α-methylpropionyloxy)ethyl group.

5. A compound according to claim 1, in which the total number of carbon atoms in $R_1$ to $R_4$ is no more than nine.

6. A compound according to claim 1, in which $R_2$ is other than hydrogen and $R_3$ is hydrogen.

7. A compound according to claim 3, in which $R_2$ and $R_4$ are each methyl and $R_3$ is hydrogen or $R_2$ is methyl and $R_3$ and $R_4$ are each hydrogen or $R_2$ is ethyl and $R_3$ and $R_4$ are each hydrogen.

8. A compound according to claim 1, being 2-ethyl-3-hydroxy-1-[2-(α-methylpropionyloxy)ethyl]pyridin-4-one or a physiologically acceptable salt thereof.

9. A compound according to claim 1 being 3-hydroxy-2,6-dimethyl-1(2-pivaloyloxyethyl)pyridin-4-one, 3-hydroxy-1-methyl-2-(2-pivaloyloxyethyl)pyridin-4-one or 1-ethyl-3-hydroxy-2-(2-pivaloyloxyethyl)pyridin-4-one or a physiologically acceptable salt thereof.

10. A compound according to claim 1 being 3-hydroxy-2-methyl-1-(2-pivaloyloxyethyl)pyridin-4-one or a phsiologically acceptable salt thereof.

11. A compound according to claim 1 being 2-ethyl-3-hydroxy-1-(2-pivaloyloxyethyl)pyridin-4-one or a physiologically acceptable salt thereof.

12. A pharmaceutical composition consisting essentially of a therapeutically effective amount of a compound of the formula (I) according to claim 1 together with a physiologically acceptable diluent or carrier.

13. A method for the treatment of a patient in need of such treatment having a toxic concentration of iron present in the body which comprises administering to that patient a therapeutically effective amount of a compound according to claim 1.

14. A method according to claim 13, in which $R_2$ is a 2-(αmethylpropionyloxy)ethyl or 2-pivaloyloxyethyl group.

15. A method according to claim 13, in which $R_1$ is a 2-(αmethylpropionyloxy)ethyl or 2-pivaloyloxyethyl group.

16. A method according to claim 13, which contains one 2-pivaloyloxyethyl group rather than one 2-(α-methylpropionyloxy)ethyl group.

17. A method according to claim 13, in which the total number of carbon atoms in $R_1$ to $R_4$ is no more than nine.

18. A method according to claim 13, in which $R_2$ is other than hydrogen and $R_3$ is hydrogen.

19. A method according to claim 15, in which $R_2$ and $R_4$ are each methyl and $R_3$ is hydrogen or $R_2$ is methyl and $R_3$ and $R_4$ are each hydrogen or $R_2$ is ethyl and $R_3$ and $R_4$ are each hydrogen.

20. A compound being a 3-hydroxypyridin-4-one of formula (I)

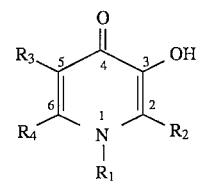

in which $R_1$ is a methyl, ethyl or 2-pivaloyloxyethyl group and $R_2$, $R_3$ and $R_4$ are each separately selected from hydrogen and methyl, ethyl and 2-pivaloyloxyethyl groups with the provisos that (a) one only of $R_1$ to $R_4$ is a 2-pivaloyloxyethyl group, (b) at least one of $R_2$ and $R_3$ is other than hydrogen and (c) the total number of carbon atoms in $R_1$ to $R_4$ is no more than eleven, the compound optionally being in the form of a physiologically acceptable salt.

21. A pharmaceutical composition consisting essentially of a therapeutically effective amount of a compound of the formula (I) according to claim 20 together with a physiologically acceptable diluent or carrier.

22. A method for the treatment of a patient in need of said treatment having a toxic concentration of iron present in the body which comprises administering to that patient a therapeutically effective amount of a compound according to claim 20.

* * * * *